(12) United States Patent
Leung et al.

(10) Patent No.: US 7,998,110 B2
(45) Date of Patent: Aug. 16, 2011

(54) MEDICAL DEVICE FOR DELIVERING DRUG AND/OR PERFORMING PHYSICAL THERAPY

(75) Inventors: Wallace Woon-Fong Leung, Hung Hom (CN); Samuel Chun-Lap Lo, Hung Hom (CN)

(73) Assignee: Hong Kong Polytechnic University, Hung-Hom, Hong Kong Sar (CN)

( * ) Notice: Subject to any disclaimer, the term of this patent is extended or adjusted under 35 U.S.C. 154(b) by 967 days.

(21) Appl. No.: 11/790,426

(22) Filed: Apr. 25, 2007

(65) Prior Publication Data

US 2008/0269570 A1    Oct. 30, 2008

(51) Int. Cl.
*A61M 31/00* (2006.01)

(52) U.S. Cl. ......................................................... 604/67

(58) Field of Classification Search ............... 604/20, 604/65–67, 131, 890.1, 19
See application file for complete search history.

(56) References Cited

U.S. PATENT DOCUMENTS 5,421,816 A    6/1995   Lipkovker
6,485,437 B1 * 11/2002   Tapper ........................... 600/573

OTHER PUBLICATIONS

Notification Concerning Transmittal of International Preliminary Report on Patentability (Forms PCT/IB/326 and PCT/IB/373) and the Written Opinion of the International Searching Authority (Form PCT/ISA/237) issued in corresponding International Application No. PCT/CN2008/070808 dated Nov. 5, 2009.

* cited by examiner

*Primary Examiner* — Manuel A Mendez
(74) *Attorney, Agent, or Firm* — Buchanan Ingersoll & Rooney PC (57) ABSTRACT

Current methods of delivering drug usually require a certain degree of human intervention. For example, a doctor, a paramedic or a patient is required to inject insulin manually when the blood sugar level becomes low. This invention provides a medical device for use with a patient for performing at least one of the functions of delivering drug and performing physical therapy to the patient. The device of this invention includes a sensor for measuring at least one parameter from the patient, an analyzer for analyzing the parameter to determine appropriate function to be carried out on the patient by said medical device, and at least one actuator to perform at least one of the functions of delivering drug and performing physical therapy.

12 Claims, 5 Drawing Sheets

MEDICAL DEVICE FOR DELIVERING DRUG AND/OR PERFORMING PHYSICAL THERAPY

FIELD OF THE INVENTION

This invention relates to medical device for use with a patient for delivering drug and/or performing physical therapy.

BACKGROUND OF THE INVENTION

Current methods of delivering drug usually require a certain degree of human intervention. For example, a doctor, a paramedic or a patient is required to inject insulin manually when the blood sugar level becomes low. In such a case, the patient's blood glucose level has to be monitored by certain devices. For arthritis attack over joints (finger joints, arm joints, knee joints or any other joints in the body), drugs may have to be applied transdermally to the affected area that could be inflamed and swollen. In such cases, the patient's joints need to be monitored by some means such as the skin temperature, symptoms of possible swell as a result of inflammation. Further, it has been found that the delivery of some drugs would be enhanced if physical therapy is applied simultaneously to patients over skin on the affected joint area. It would be advantageous if the patient can be treated by suitable drug administration and/or physical therapy at the right time. However, to the best of the inventors' knowledge, there is no existing device catering this need.

OBJECTS OF THE INVENTION

Therefore, it is an object of this invention to provide medical devices that can delivery drug and/or provide physical therapy to a patient at appropriate time. It is also an object of this invention to resolve at least one or more of the problems as set forth in the prior art. As a minimum, it is an object of this invention to provide the public with a useful choice.

SUMMARY OF THE INVENTION

Accordingly, this invention provides a medical device for use with a patient for performing at least one of the functions of delivering drug and performing physical therapy to the patient including:
  at least one sensor for measuring at least one parameter from the patient;
  an analyzer for analyzing the parameter to determine appropriate function to be carried out on the patient by said medical device; and
  at least one actuator to perform at least one of the functions of delivering drug and performing physical therapy.

Preferably, the medical device of this invention may further include a drug storage unit for storing at least one drug, said drug storage unit being operatively connected to the actuator for delivering said drug to the patient.

Preferably, the parameter is selected from the group consisting of electrical current or resistance, temperature, pressure, tension, humidity, flow circulation in blood vessels, pH, intensity of at least one predetermined wavelength of electromagnetic wave, sonic signal, concentration of at least one chemical compound, and their combinations thereof. More preferably, the chemical compound is selected from the group consisting of glucose, sodium chloride, dimethyl sulfoxide, azone, isopropyl myristate, propylene glycol, Carbomer resins, gelling agents and their combinations thereof.

Advantageously, the physical therapy is selected from the group consisting of mechanical stimulus, thermal stimulus, electrical stimulus, ultrasonic stimulus, magnetic stimulus, and irradiation of at least one predetermined wavelength.

Additionally, the medical device of this invention may further include attachment means for attaching the medical device to the patient.

BRIEF DESCRIPTION OF THE DRAWINGS

Preferred embodiments of the present invention will now be explained by way of example and with reference to the accompanying drawings in which.

DETAILED DESCRIPTION OF THE PREFERRED EMBODIMENTS

This invention is now described by way of example with reference to the figures in the following paragraphs. List 1 is a part list so that the reference numerals in the figures may be easily referred to.

Objects, features, and aspects of the present invention are disclosed in or are apparent from the following description. It is to be understood by one of ordinary skilled in the art that the present discussion is a description of exemplary embodiments only, and is not intended as limiting the broader aspects of the present invention, which broader aspects are embodied in the exemplary constructions.

Figure 1:
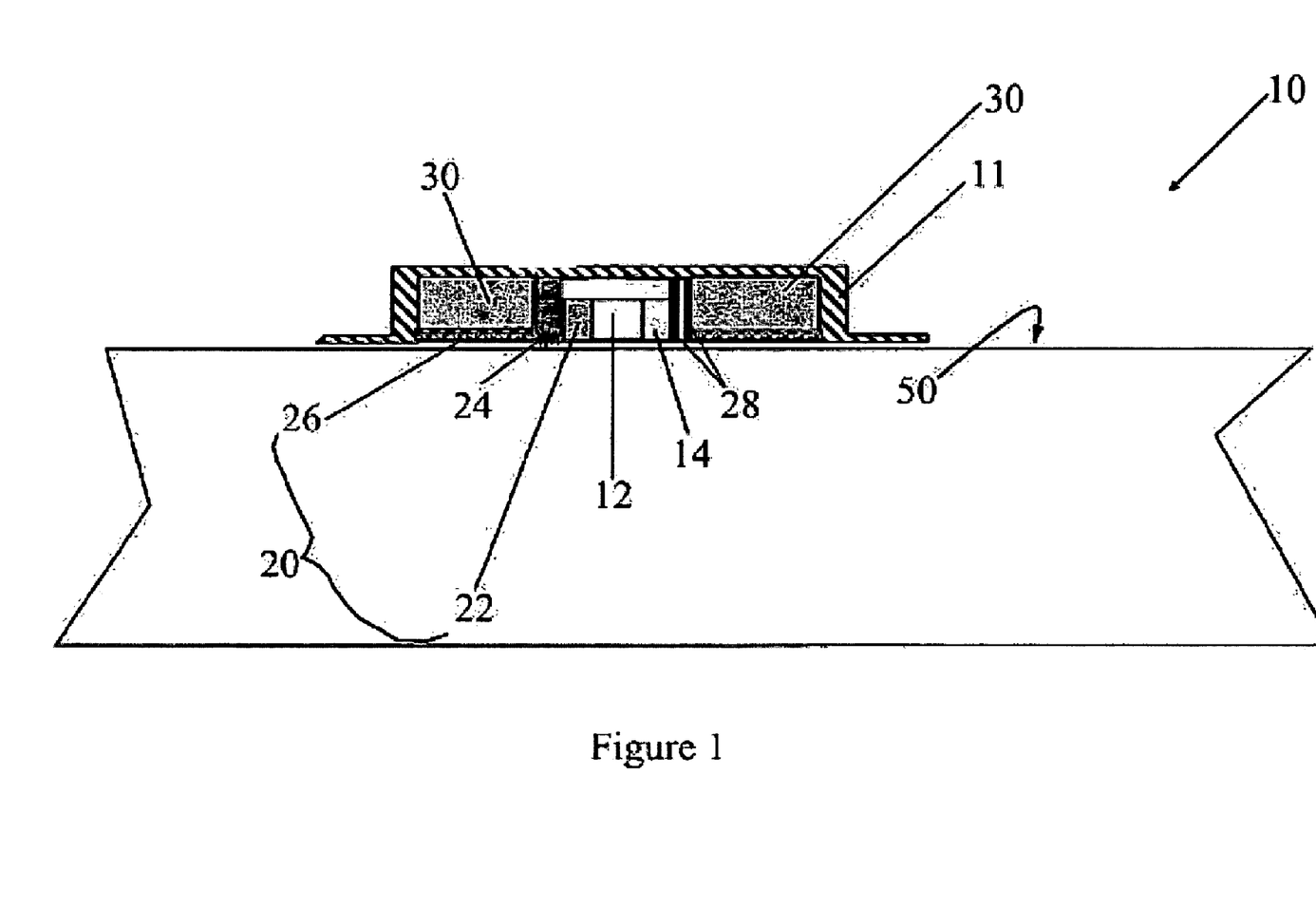
FIG. 1 shows the construction of a medical device of this invention.

FIG. 1 shows a medical device (10) of this invention, which is in contact with the skin 50 of a patient. The device has at least one sensor (12) for measuring at least one parameter from the patient. Some parameters, for example temperature, relative humidity, pH, and concentration of medication/drug/salts/fatty acid on the skin, can be measured from the skin of the patient. Conventional sensors can be used for obtaining these parameters. For example, the following sensors can be used for this invention:

Temperature Sensor

A temperature sensor is used to measure the temperature on the skin surface. Temperature can be one of the parameters to determine the appropriate time to deliver the medicine to the treated area based on the elevation in local skin temperature beyond a certain threshold. A thermal couple can be used associated with another temperature sensor for cold junction reference to the ambient environment.

Another type of temperature sensor is the transistor type sensor wherein it makes use of the fact that resistivity of the transistor changes with temperature. By monitoring the resistivity, the temperature can be deduced.

Pressure Sensor

The contact pressure applied by a cuff to the treated area will increase when there is inflammation on the treated area. A force sensor is applied to measure this pressure difference between inflamed and normal situations. This force sensor can be made of a semiconductor material, for example silicon, which will change its resistance when a force is applied. A constant voltage is applied to measure the variation in electrical current, which reflects the force change on the contact area.

Humidity Sensor

A humidity sensor is used to measure the local moisture above the skin surface when the medicine is applied. This information can be used as a parameter to optimize the drug delivery time, dose, and rate. A relative humidity sensor is made of a capacitor with polymer as a dielectric material. This polymer will change its dielectric constant when absorbing moisture, hence, variation in the measured capacitance of the capacitor reflects the humidity change. This capacitance difference will be translated to an electrical voltage by a driving circuit as a measurement of humidity change.

The constructions of these sensors are known in the art, and therefore, would not be further discussed here.

Other parameters, for example, concentration of chemicals including arthritis drug and/or insulin, on skin surface could be measured by a suitable sensor to determine the penetration rate of the chemical through the skin. There are existing sensors that can create minimal discomfort to the patient when measuring these parameters. For example, many existing devices for measuring blood glucose level of patients suffering from diabetes can create less discomfort in most cases. The sensor would be specific for a given chemical.

Gelling agents and Carbomer resins could also be detected by suitable sensors. Gelling agents are additives (usually in powder form) used to thicken and stabilize various liquid preparations, for example cosmetic cream. These gelling agents are usually hygroscopic in nature. When added to various liquid preparations, these polymers can swell to many times their original volume as they can absorb and retain water. Such swollen particles remain discrete in various mucilaginous or colloidal dispersions. The gelling agents provide the liquid with texture through formation of a gel. On the other hand, a gel is a colloidal system in which a porous network of interconnected particles spans the volume of a liquid medium. In general, gels are apparently solid, jelly-like materials. Both by weight and volume, gels are mostly liquid in composition and thus exhibit densities similar to liquids, however have the structural coherence of a solid. An example of a common gel is edible gelatin. Typical gelling agents include natural gums, starches, pectins, agar-agar and gelatin. Often they are based on polysaccharides or proteins. Further examples of gelling agents include:

Alginic acid (E400), sodium alginate (E401), potassium alginate (E402), ammonium alginate (E403), calcium alginate (E404)—polysaccharides from brown algae Agar (E406, a polysaccharide obtained from red seaweeds)

Carrageenan (E407, a polysaccharide obtained from red seaweeds)

Locust bean gum (E410, a natural gum from the seeds of the Carob tree)

Pectin (E440, a polysaccharide obtained from apple or citrus-fruit)

Gelatine (E441, made by partial hydrolysis of animal collagen)

Carbomer 940 is a specific type of resins of the Carbomer series that is commonly used in cosmotic industry and acted as an emulsifying agent. These resins have low toxicity. These Carbomer resins (-910, -934, -934P, -940, -941, and -962) are synthetic, high molecular weight, nonlinear polymers of acrylic acid cross-linked with a polyalkenyl polyether. They are chemically similar to each other, differing only in ascending molecular weights (which range from Carbomer-910 to Carbomer-962). They contain between 98.7% and 99.9% acrylic acid. When dried at 80° C. for one hour, they contain not less than 56.0% and not more than 68.0% carboxylic acid (—COOH) groups. The general structural formula is:

Further details of Carbomer resins can be found in the article "Final Report on the Safety Assessment of Carbomers-934, -910, -934P, -940, -941, and -962" in "Polymers for Personal Care", which is incorporated herein as a reference.

Although the size of the sensors (12) should not affect the working of this invention, it would be apparent to a person skilled in the art that compact sensors are generally preferred. Some pressure, temperature and humidity sensors are made from micro-electrical mechanical systems MEMS and typically these are very small on the order of a few millimeter square and several millimeter thick. They can be conveniently incorporated into the system without taking much room and causing discomfort to users. Suitable sensors may include NTC Thermistor EC95 (thermocouple) from GE™, AD590 series from Analog Devices™, and FOT-HERO from Fiso Technologies for sensing temperatures; PX305/315 series from Omega™ and NPC-100 from GE™ for sensing pressure; Capactive SMD humidity sensor HC103/105 and HMX2200 from Hygometrix™ for sensing humidity.

Figure 2:
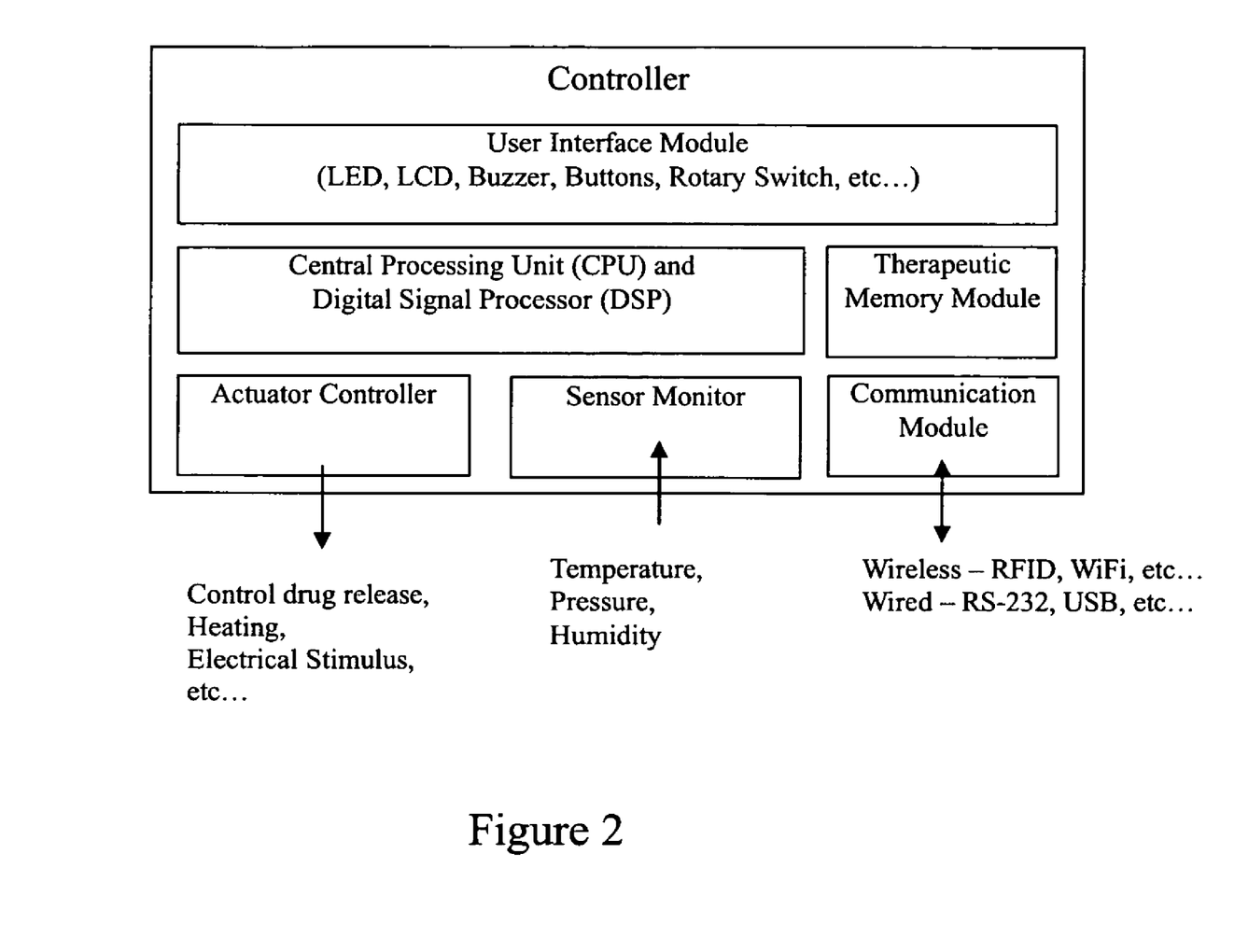
FIG. 2 shows the logical structure of the controller in association with the actuator, sensor, and the communication module of the medical device of this invention.
Figure 3:
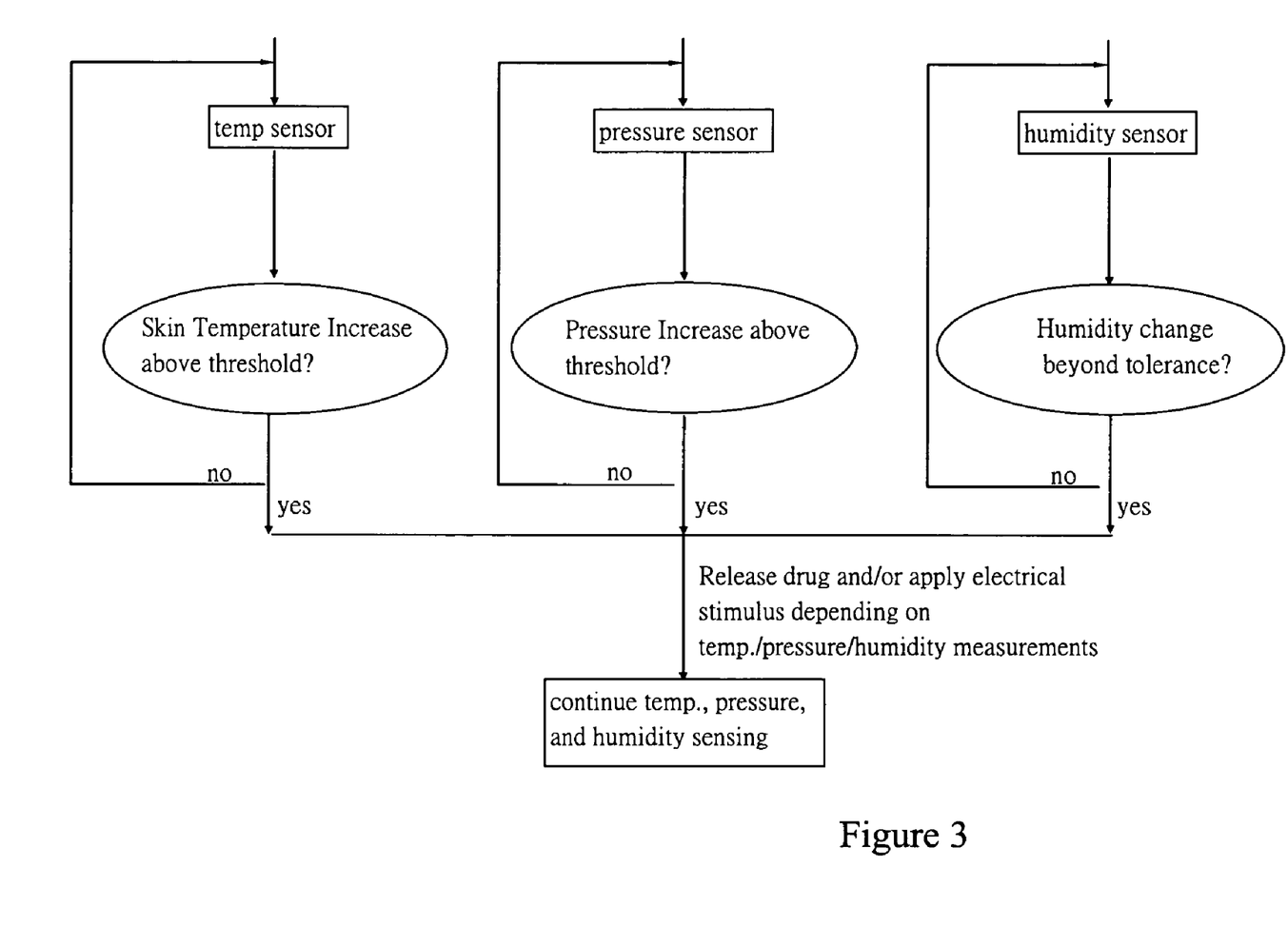
FIG. 3 shows the flowchart of the operation of the sensors and the actuators of the device of this invention.

The medical device (10) further includes an analyzer or controller (14) for analyzing the information obtained from the sensor (12), and determining what actions from the medical device are required to be performed on the patient. The controller (14) may be in the form of analog/digital converter, signal processor, microcontroller or CPU with suitable analog/digital converter and signal processor. The logical structure of the controller (14) is shown in FIG. 2. After the parameters are measured and collected by the sensor (12), the parameters will then be analyzed by the controller (14). The controller (14) will then determine appropriate actions to be performed on the patient by the medical device (10) according to the analysis. Temperature, pressure, and humidity are measured by the respective sensors. When each of these measurements exceeds the predetermined threshold or tolerance levels, drug and or electrical stimulus could be applied to the affected area to sooth pain and reduce temperature of swollen area from inflammation due to arthritis attack. FIG. 3 shows a flowchart of the operation of the sensors and the actuators of the device of this invention. The threshold levels would be determined by a person skilled in the art according to the different operation environment or the needs of the patient.

The controller (14) can be an embedded system programmed with different types of therapies depending on the disease and the medical history of a given patient. The medical device (10) can perform specific therapy by sensing the patient's status, stimulates the patient by actuators (20), and logs the progress/status using internal memory. It can also be equipped with communication units, and user interface to facilitate the therapy purpose. Details of the controller (14) are explained as follows:

User Interface Module

The User Interface Module is responsible for presenting the users the real-time or historical system status such as sensor values, therapeutic programs, etc. . . . , by means of LED, LCD, and buzzers, etc. . . . . It is also responsible for accepting user inputs such as emergency stops, therapy activations, etc. . . . by means of button presses, rotary switch, etc. . . . . . It is controlled and monitored by the Central Processing Unit to give the user a facility to interface with the Smart Device.

Central Processing Unit (CPU) and Digital Signal Processor (DSP)

The CPU is responsible for the coordination of the User Interface Module, the Therapeutic Memory Module, the Actuator Controller, the Sensor Monitor, and Communication Module to perform a therapy sessions. The DSP is to perform the mathematical calculations and decision-making algorithms to realize an adaptable therapy session.

Therapeutic Memory Module

The Therapeutic Memory Modules is responsible for the storage of the information for the Controllers relating primary to therapeutic information. The therapeutic information may have mainly 2 types. The 1st type is the preset therapy programs that are preloaded by users via the Communications Module. The 2nd type can be the therapy that is automatically adaptable to the ongoing therapy progress of the patients. The adaptation methods and outcomes are based on the mathematical calculations and decision-making algorithms of the CPU and DSPs. The therapy progress is monitored by calculating the variation gradient of the vital signs taken from the sensors, including those for detecting temperature, pressure, humidity, and pH. A proper therapy program will be selected from the pre-loaded therapy programs based on the calculated variation gradient of vital signs. The selection criteria can be of 2 folds. The first one is based on the clinical study from a group of patients to decide the proper drug dosage and electrical stimulus therapy for patients on different stages of improvement by applying the therapy. These criteria can be updated from the most recent clinical study to provide a better treatment for individual patients. The second one is based on the patients individual healing condition. The Therapeutic Memory Module shall correlated the healing condition, based on the sensors, and the therapeutic effect, based on drug dosage and electrical stimulus intensity; and formulates a personal treatment that adapts to a patients vital signs response to the treatment.

Figure 4:
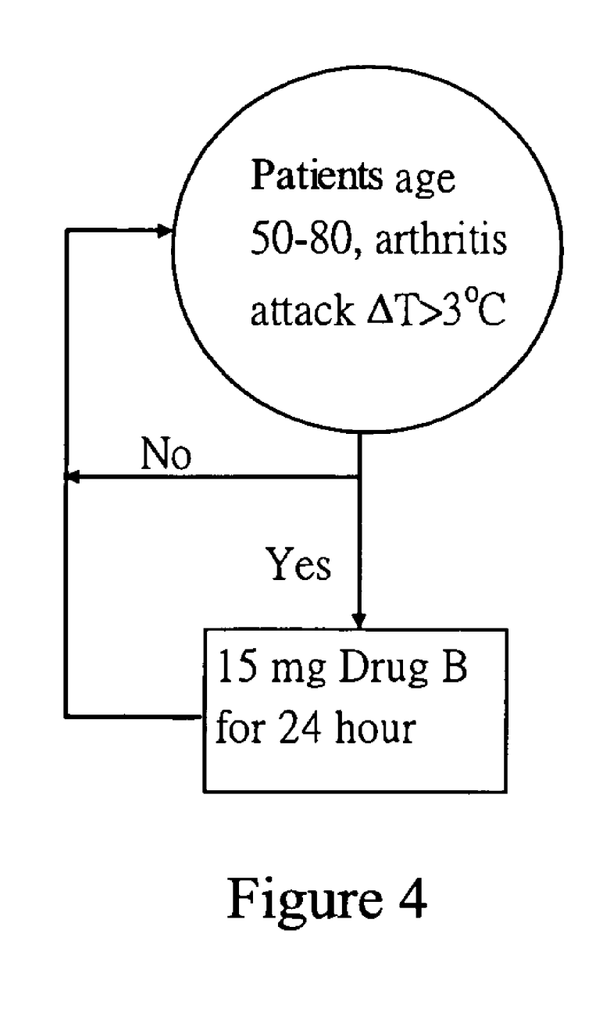
FIG. 4 shows exemplary preload therapy algorithms based on temperature difference between affected area and normal area of body.

FIG. 4 shows an exemplary preload therapy where all patients of ages 50-80 when under arthritis attack with measured temperature difference between arthritis affected area and normal area more than 3 degree Celsius, then medication Drug B of 15 mg is applied over the affected area.

Figure 5:
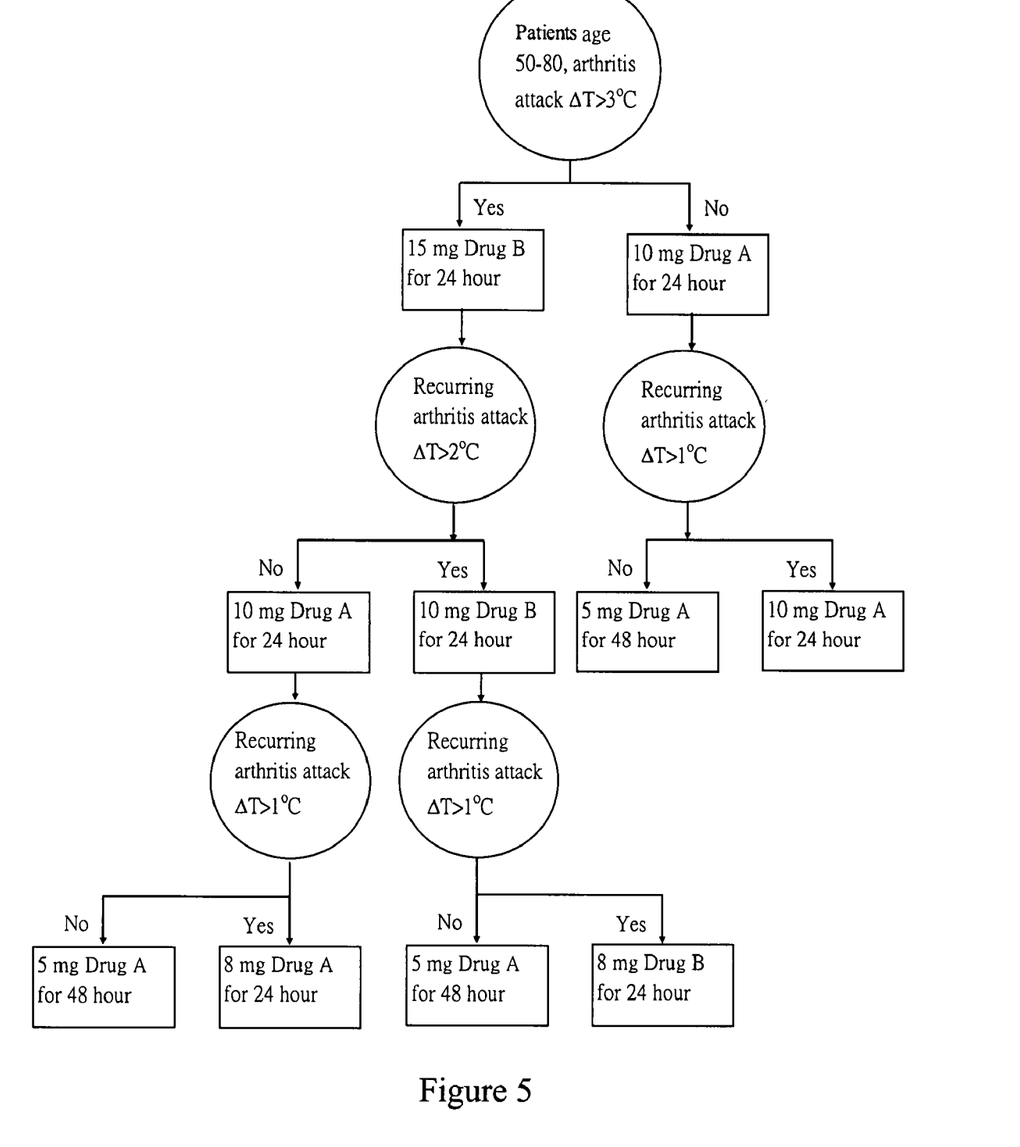
FIG. 5 shows exemplary therapy algorithms based on patients individual healing condition with conditions reflected by temperature difference between affected and normal areas of the body.

On the other hand, medication and dosage are applied based on individual's healing condition which is indicated by the temperature difference between affected area and normal area as shown in FIG. 5. This procedure can be applied to any patient once the rules above are followed.

Communication Module

The Communication Module is purely optional, and is responsible for gathering and delivering the information of the Controller from/to the external machine, such as PC, RFID-reader/writer, etc. . . . , via wired and wireless means. It can be used for downloading therapy program, uploading therapy progress, and conveying Smart Device identity and capability, etc.

Actuator Controller

The Actuator Controller is to control the actuator such as drug release, heater, and electrical stimulator in a timely and organized manner. The actuator of the drug can be a syringe pump, a rotary pump, a micro diaphragm pump, or a cartridge with back pressure and a valve to control its fluid releasing time. The selection of the pump could be based on the viscosity of the drug fluid and the required fluid flow rate. The syringe pump can be driven by a stepper motor with gear set to convert the rotary motion to the linear for pushing the plunger of the syringe forward or pulling it backward. This can pump or refill the drug to the syringe. A rotary pump can also be driven by a stepper motor with rotation of the gears to provide the required pumping force to the drug fluid. A micro diaphragm pump can be based on the vibration of a unimorph piezoelectrical metal disk to provide the actuation force, which pushes/pulls the fluid out of/into the pump chamber. The electronic pump drivers of the various pumps would be controlled by the microcontroller from the CPU.

The actuation of the electrical stimulator can be initiated by a pulsed electrical voltage in, for example, the 70 to 90 volts high voltage range with connection to the skin treating location by a pair of conductive electrodes, for example graphite rubber pad or stainless steel fiber fabric. The high pulsed voltage can be boosted from a battery voltage by a boost converter circuit. The input digital signal of the driver circuit can also be provided from the microcontroller from the CPU, which performs as a central unit to control the drug release, the electrical stimulator, and the heater with digital signal feeding to the required actuator driver. The heater can be provided by joule heating from a conductive metal wire with designed heating power and area coverage with proper thermal and electrical isolation.

Sensor Monitoring

The Sensor Monitor is to collect the sensing value of sensors such as temperature, pressure and humidity in a timely and organized manner.

For performing the required actions on the patient, the medical device (10) has at least one actuator (20), which can exist in various different forms. Suitable actuators (20) include drug delivering devices in the form of injection device (22) or permeable membrane and valve (26), heater (24), electrodes (28), magnetic field generator (not shown in the figure), optical actuator (including Infra-red, ultraviolet), and sonic actuator including ultrasound. Providing actuators including heater (24), electrodes (28), magnetic field generator, optical actuator or sonic actuator (including ultrasound) may allow physical therapies to be performed in conjunction with drug delivery, which may enhance the overall therapeutic effects. Details of particularly preferred actuators are described as follows.

Syringe Pump

A syringe pump can be used to pump the medicine fluid to the required treated area. It can be made of two parts. The first part is a syringe, which is similar to the regular syringe having a medicine container and a movable piston. As the piston moves forward, the enclosed volume of the syringe container is decreased and a controlled volume of the liquid medicine is ejected. To move the piston automatically, a linear motor, which is the second part, is provided. A piezoelectric linear motor is preferred for its miniature size and minimal number of parts, which can be made of a screw shaft and a nut attached with piezoelectric pads. When two opposite sides of the piezoelectric pads are actuated by two sinusoidal electrical voltage waves with half-wave phase shift, a hula-hoop motion on the screw nut is generated, rotating the screw shaft and moving it forward or backward depending on the electrical control. A control circuitry with microcontroller on printed circuit board (PCB) can be used to drive the linear motor.

Micro Pump

A micro pump is another option for pumping liquid medicine to the treated area. Unlike a syringe pump, it separates the medicine cartridge from the pumping mechanism, which might ease the process of refilling the medicine by simply changing a new cartridge. A micro pump can be made of a piezoelectric actuated membrane with two valves, one on inlet and another one on outlet. As the membrane bending upward to increase the volume of the pump chamber, the inlet valve is opened and the outlet valve is closed to fill the pump chamber with a controlled volume. As the membrane bending downward to decrease the volume of the pump chamber, the inlet valve is closed and the outlet valve is opened to pump the liquid out of the chamber. These two processes cycle the liquid through the pump chamber to continuous pumping the liquid from the inlet to the outlet.

Electrical Stimulus Device

The electro-stimulus device senses skin electrical resistance/current and applies a voltage to stimulate the nerve endings. An electric field/voltage will be applied in appropriate place in the sock to stimulate the local nerve endings and treat the inflamed area of the body.

Heater Pad

A heater pad is made of a metal wire actuated by joule heating, which can generate heat by passing an electrical current through the metal wire. This metal can be arranged in a planar serpentine shape to cover the required heating area, and a cloth to distribute the heat uniformly to the treated area.

Magnetic Device

It is known that muscles can be relaxed in the presence of a weak magnetic field over the body. This relaxed portion could also have an added benefit of improving diffusion of drugs over skin with increased pore size and thus skin permeability. The magnetic field can be provided by a permanent magnet with a constant magnetic field or a magnetic coil to control the magnetic field by varying its electrical current.

Ultrasonic Device

A small device for generating ultrasound at mega hertz range, from 1 to 3 MHz, could be used to sooth the patient's body, including the reduction of pain on the joints. When ultrasonic waves are transmitted to the tissue, a thermal effect would be generated to reduce inflammation, and the mobility and flexibility of the joints could also be increased. The ultrasonic transducer can be formed by piezoelectric composite materials. By applying an ac voltage to actuate the piezoelectric composite materials, an ultrasonic wave can be generated.

UV Conversion Device

There are garments or fabrics that absorb ultraviolet light from the sun and converted photons to infra-red emission that could be helpful in treating the body with thermal healing effect.

The construction of the above actuators is generally known in the art, and therefore, will not be described further.

The medical device (10) of this invention may include a removable drug cartridge (30) operably connected to the injection device (22) or permeable membrane and valve (26). The removable drug cartridge (30) contains the drug to be delivered to the user. The medical device (10) can have more than one removable drug cartridge (30). Although may be unified with the medical device (10) of this invention, the drug cartridge (30) is preferred to be removable for the ease of replenishment of drugs.

The medical device (10) of this invention can allow suitable therapies in the form of drug delivery and/or physical therapies to be delivered to a patient at fixed time interval or according to the condition(s) of the patient as sensed by the sensors (12). This may provide improved effect over existing methods as therapies can be delivered to the patient at appropriate times.

While the preferred embodiment of the present invention has been described in detail by the examples, it is apparent that modifications and adaptations of the present invention will occur to those skilled in the art. Furthermore, the embodiments of the present invention shall not be interpreted to be restricted by the examples or figures only. It is to be expressly understood, however, that such modifications and adaptations are within the scope of the present invention, as set forth in the following claims. For instance, features illustrated or described as part of one embodiment can be used on another embodiment to yield a still further embodiment. Thus, it is intended that the present invention cover such modifications and variations as come within the scope of the claims and their equivalents.

| List 1 | |
| --- | --- |
| Reference Numerals | Description |
| 10 | Medical device |
| 12 | Sensor |
| 14 | Controller |
| 20 | Actuators |
| 24 | Heater |
| 26 | Semi-permeable membrane and/or valve |
| 28 | Electrodes |
| 30 | Removable drug storage |
| 50 | Skin of an user |

The invention claimed is:

1. A medical device for use with a patient for performing at least one of the functions of delivering a drug and applying a physical therapy to the patient, the device including:
   at least one sensor for measuring at least one parameter of the patient, wherein the at least one parameter is indicative of a pain and an inflammation being experienced by the patient;
   an analyzer for analyzing the parameter to determine appropriate function to be carried out on the patient by said medical device; and
   at least one actuator to perform at least one of the functions of delivering the drug and applying the physical therapy in response to the analyzed parameter.

2. The medical device of claim 1 further including a drug storage unit for storing at least one drug, said drug storage unit being operatively connected to the actuator for delivering said drug to the patient.

3. The medical device of claim 1, wherein the parameter is selected from a group including electrical current or resistance, temperature, pressure, tension, humidity, flow circulation in blood vessels, pH, intensity of at least one predetermined wavelength of electromagnetic wave, sonic signal, concentration of at least one chemical compound, and their combinations thereof.

4. The medical device of claim 3, wherein said chemical compound is selected from a group including glucose, sodium chloride, dimethyl sulfoxide, azone, isopropyl myristate, propylene glycol, Carbomer resins, gelling agents and their combinations thereof.

5. The medical device of claim 1, wherein the physical therapy is selected from a group including mechanical stimulus, temperature stimulus, electrical stimulus, ultrasonic stimulus, magnetic stimulus, and irradiation of at least one predetermined wavelength.

6. The medical device of claim 1 including an attachment means for attaching the medical device to the patient.

7. A method for use with a patient for performing at least one of the functions of delivering a drug and applying a physical therapy to the patient using a medical device, said method including the steps of:

measuring at least one parameter of the patient, wherein the at least one parameter is indicative of a pain and an inflammation being experienced by the patient;

analyzing the parameter to determine an appropriate function to be carried out on the patient; and performing at least one of the functions of delivering the drug and applying the physical therapy in response to the analyzed parameter.

8. The method of claim 7 wherein the medical device includes a drug storage unit for storing at least one drug, said drug storage unit being operatively connected to the actuator for delivering said drug to the patient.

9. The method of claim 7, wherein the parameter is selected from a group including electrical current or resistance, temperature, pressure, tension, humidity, flow circulation in blood vessels, pH, intensity of at least one predetermined wavelength of electromagnetic wave, sonic signal, concentration of at least one chemical compound, and their combinations thereof.

10. The method of claim 9, wherein said chemical compound is selected from a group including glucose, sodium chloride, dimethyl sulfoxide, azone, isopropyl myristate, propylene glycol, Carbomer resins, gelling agents and their combinations thereof.

11. The method of claim 7, wherein the physical therapy is selected from a group including mechanical stimulus, temperature stimulus, electrical stimulus, ultrasonic stimulus, magnetic stimulus, and irradiation of at least one predetermined wavelength.

12. The method of claim 7 further including the step of attaching the medical device to the patient by an attachment means.

* * * * *